(12) United States Patent
Sundermann et al.

(10) Patent No.: US 7,476,763 B2
(45) Date of Patent: Jan. 13, 2009

(54) OXO-SUBSTITUTED CYCLOHEXYL-1,4-DIAMINE COMPOUNDS

(75) Inventors: Corinna Sundermann, Aachen (DE); Bernd Sundermann, Aachen (DE)

(73) Assignee: Gruenenthal GmbH, Aachen (DE)

( * ) Notice: Subject to any disclaimer, the term of this patent is extended or adjusted under 35 U.S.C. 154(b) by 163 days.

(21) Appl. No.: 11/594,952

(22) Filed: Nov. 9, 2006

(65) Prior Publication Data

US 2007/0088034 A1   Apr. 19, 2007

Related U.S. Application Data

(63) Continuation of application No. PCT/EP2005/004907, filed on May 6, 2005.

(30) Foreign Application Priority Data

May 10, 2004   (DE) .................... 10 2004 023 501

(51) Int. Cl.
  *C07C 233/05* (2006.01)
  *A61K 31/65* (2006.01)

(52) U.S. Cl. ............... 564/154; 514/241; 514/252.1; 514/248; 514/310; 514/311; 514/357; 514/359; 514/367; 514/372; 514/374; 514/378; 514/383; 514/394; 514/396; 514/406; 514/419; 514/443; 514/469; 514/538; 514/563; 514/621; 544/209; 544/237; 544/333; 544/336; 546/146; 546/159; 548/267.2; 548/335.5; 549/76; 560/45; 562/463; 564/169

(58) Field of Classification Search ................ 514/241, 514/252.1, 248, 310, 311, 357, 359, 367, 514/372, 374, 378, 383, 394, 396, 406, 419, 514/443, 469, 538, 563, 621; 544/209, 237, 544/333, 336; 546/146, 159; 548/152, 190, 548/214, 223, 257, 267.2, 335.5; 549/76; 560/45; 562/463; 564/154, 169

See application file for complete search history.

(56) References Cited

U.S. PATENT DOCUMENTS

| 5,304,479 A | 4/1994 | Lin et al. |
|---|---|---|
| 2003/0029119 A1 | 2/2003 | Coleman |
| 2003/0236250 A1 | 12/2003 | Castro et al. |
| 2004/0229872 A1 | 11/2004 | Friderichs et al. |
| 2005/0245593 A1 | 11/2005 | Sundermann et al. |

FOREIGN PATENT DOCUMENTS

| WO | WO 02/090317 A1 | 11/2002 |
|---|---|---|
| WO | WO 2004/043899 A1 | 5/2004 |

*Primary Examiner*—Shailendra Kumar
(74) *Attorney, Agent, or Firm*—Crowell & Moring LLP

(57) ABSTRACT

Novel cyclohexyl-1,4-diamine compounds corresponding to formula I:

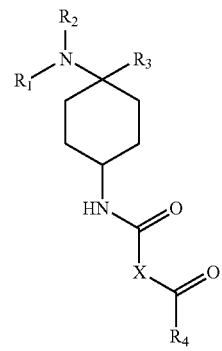

methods for their production, pharmaceutical formulations containing these compounds, methods of producing such pharmaceutical formulations and related methods of treating or inhibiting certain diseases or conditions.

24 Claims, No Drawings

OXO-SUBSTITUTED CYCLOHEXYL-1,4-DIAMINE COMPOUNDS

CROSS-REFERENCE TO RELATED APPLICATIONS

This application is a continuation of International patent application Serial No. PCT/EP2005/004907 filed May 6, 2005 which claims benefit to German patent application Serial No. 10 2004 023 501.5 filed May 10, 2004, the entire disclosures of which are hereby incorporated in their entirety.

FIELD OF THE INVENTION

The present invention relates to substituted cyclohexyl-1,4-diamine compounds, to processes for the production thereof, to pharmaceutical formulations containing these compounds, to methods of producing such pharmaceutical formulations and to related methods of treating or inhibiting certain diseases or conditions.

BACKGROUND OF THE INVENTION

The treatment of chronic and non-chronic pain conditions has great importance in medicine. There is a worldwide need for effective methods of treating pain. The urgent need for action for patient-oriented and purposeful treatment of chronic and non-chronic pain conditions, this being taken to mean the successful and satisfactory treatment of pain for the patient, is documented in the large number of scientific papers which have recently appeared in the field of applied analgesics and fundamental research work on nociception.

Conventional μ-opioids such as morphine are very effective in the treatment of strong to very strong pain and are of great importance for the treatment of pain. However, it may be advantageous if, in addition to the μ-opioid receptor, further opioid receptors, in particular the ORL1 receptor, are affected, since pure μ-opioids also have undesirable side effects, such as obstipation and respiratory depression, and may also lead to addiction. The opioid receptors δ, κ and ORL1 are also involved in the state of pain (Opioids: Introduction, pp. 127-150, Further Opioid Receptors, 455-476 in: Analgesics—From Chemistry and Pharmacology to Clinical Application, Wiley VCH, 2002).

It is also known that influencing of serotonin and/or noradrenalin re-uptake can be beneficial to the effects and side effects of opioids (Example: Tramadol, see Opioids with Clinical Relevance: Tramadol, 228-230 in: Analgesics—From Chemistry and Pharmacology to Clinical Application, Wiley VCH, 2002).

The ORL1 receptor is also involved in the regulation of further physiological and pathophysiological processes. These include inter alia learning and memory formation (Manabe et al, Nature, 394, 1997, pp. 577-581), Hörvermögen [Hearing capacity] (Nishi et al, EMBO J., 16, 1997, pp. 1858-1864) and numerous further processes. In a synopsis by Calo et al (Br.J. Pharmacol., 129, 2000, 1261-1283) there is an overview of the indications or biological procedures, in which the ORL1 receptor plays a part or could highly probably play a part. Mentioned inter alia are: analgesics, stimulation and regulation of nutrient absorption, effect on μ-agonists such as morphine, treatment of withdrawal symptoms, reduction of the addiction potential of opioids, anxiolysis, modulation of motor activity, memory disturbances, epilepsy; modulation of neurotransmitter release, in particular of glutamate, serotonin and dopamine, and therefore neurodegenerative diseases; influencing the cardiovascular system, triggering an erection, diuresis, anti-natriuresis, electrolyte balance, arterial blood pressure, water-retention disorders, intestinal motility (diarrhea), relaxation of the respiratory tract, micturation reflex (urinary incontinence). The use of agonists and antagonists such as anoretics, analgesics (also when administered with opioids) or nootropics will also be discussed.

Structurally related compounds which have an affinity with the ORL1 receptor are known from the prior art (WO 02090317). The effect on noradrenalin and serotonin re-uptake has not previously been described for this structural class.

SUMMARY OF THE INVENTION

An object of the present invention was to provide pharmaceutical compositions which act on the opioid receptor system and are thus suitable for pharmaceutical compositions, in particular for the treatment of the various diseases associated with this system according to the prior art and for use in the indications mentioned therein. The compounds are also intended to influence noradrenalin and serotonin re-uptake.

The invention therefore relates to substituted cyclohexyl-1,4-diamine compounds of general formula I,

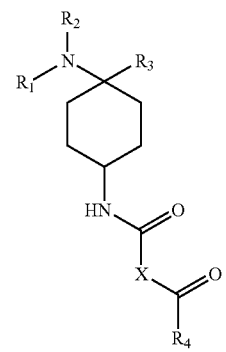

wherein $R^1$ and $R^2$ independently of one another represent H; respectively saturated or unsaturated, branched or unbranched, singly or multiply substituted or unsubstituted $C_{1-5}$ alkyl; respectively singly or multiply substituted or unsubstituted $C_{3-8}$-cycloalkyl; or respectively singly or multiply substituted or unsubstituted aryl, $C_{3-8}$ cycloalkyl or heteroaryl bound by $C_{1-3}$ alkyl;

or the radicals $R^1$ and $R^2$ together represent $CH_2CH_2OCH_2CH_2$, $CH_2CH_2NR^{10}CH_2CH_2$ or $(CH_2)_{3-6}$, wherein $R^{10}$ represents H; respectively saturated or unsaturated, branched or unbranched, singly or multiply substituted or unsubstituted $C_{1-5}$ alkyl; respectively singly or multiply substituted or unsubstituted $C_{3-8}$ cycloalkyl; respectively singly or multiply substituted or unsubstituted aryl or heteroaryl; or respectively singly or multiply substituted or unsubstituted aryl, $C_{3-8}$ cycloalkyl or heteroaryl bound by $C_{1-3}$ alkyl; respectively substituted or unsubstituted C(O)phenyl, C(O)heteroaryl, C(O)$C_{1-5}$ alkyl;

$R^3$ represents respectively saturated or unsaturated, branched or unbranched, singly or multiply substituted or unsubstituted $C_{1-5}$ alkyl; respectively singly or multiply substituted or unsubstituted $C_{3-8}$ cycloalkyl; respectively unsubstituted or singly or multiply substituted aryl or heteroaryl;

respectively unsubstituted or singly or multiply substituted aryl, heteroaryl or $C_{3-8}$ cycloalkyl bound by a $C_{1-3}$ alkyl group;

X represents a branched or unbranched, unsubstituted or singly or multiply substituted alkyl chain $(CH_2)_n$, aryl or $C_{3-8}$ cycloalkyl, or respectively substituted or unsubstituted aryl or $C_{3-8}$ cycloalkyl bound by a $C_{1-3}$ alkyl chain, where n=0, 1, 2, 3, 4, 5, $R^4$ represents respectively saturated or unsaturated, branched or unbranched, singly or multiply substituted or unsubstituted $C_{1-5}$ alkyl; respectively singly or multiply substituted or unsubstituted $C_{3-8}$ cycloalkyl; respectively singly or multiply substituted or unsubstituted aryl or heteroaryl; or respectively singly or multiply substituted or unsubstituted aryl, $C_{3-8}$ cycloalkyl or heteroaryl bound by $C_{1-3}$ alkyl, in the form of the racemate; the enantiomers, diastereomers, mixtures of the enantiomers or diastereomers or an individual enantiomer or diastereomer; the bases and/or salts of physiologically acceptable acids or cations.

The compounds according to the invention exhibit good binding to the μ receptor and the ORL1 receptor, but also to other opioid receptors. Surprisingly it has been found that the compounds are also good inhibitors of noradrenalin and serotonin re-uptake. They are therefore also suitable for treating depression and/or bulimia and/or anorexia and/or catalepsy and/or anxiolysis and/or increasing alertness and/or libido.

The terms "$C_{1-5}$ alkyl" and "$C_{1-3}$ alkyl" comprise, in the context of this invention, acyclic saturated or unsaturated hydrocarbon radicals, which may be branched or straight-chained and unsubstituted or singly or multiply substituted, with 1, 2, 3, 4 or 5 C atoms or 1, 2 or 3 C atoms, i.e. $C_{1-5}$ alkanyls, $C_{2-5}$ alkenyls and $C_{2-5}$ alkynyls or $C_{1-3}$ alkanyls, $C_{2-3}$ alkenyls and $C_{2-3}$ alkynyls. Alkenyls have at least one C—C double bond and alkynyls at least one C—C treble bond. Alkyl is advantageously selected from the group comprising methyl, ethyl, n-propyl, 2-propyl, n-butyl, iso-butyl, sec.-butyl, tert.-butyl, n-pentyl, iso-pentyl, neo-pentyl, ethylenyl (vinyl), ethynyl, propenyl (—CH$_2$CH═CH$_2$, —CH═CH—CH$_3$, —C(═CH$_2$)—CH$_3$), propinyl (—CH—C≡CH, —C≡C—CH$_3$), 1,1-dimethylethyl, 1,1-dimethylpropyl, butenyl, butynyl, pentenyl and pentynyl.

For the purposes of this invention, the term "cycloalkyl" or "$C_{3-8}$ cycloalkyl" means cyclic hydrocarbons with 3, 4, 5, 6, 7 or 8 carbon atoms, wherein the hydrocarbons may be saturated or unsaturated (but not aromatic), unsubstituted or singly or multiply substituted. With respect to cycloalkyl, the term also comprises saturated or unsaturated (but not aromatic) cycloalkyls, in which one or two carbon atoms are replaced by an S, N or O heteroatom. $C_{3-8}$ cycloalkyl is advantageously selected from the group comprising cyclopropyl, cyclobutyl, cyclopentyl, cyclohexyl, cycloheptyl, cyclooctyl, cyclopentenyl, cyclohexenyl, cycloheptenyl and cyclooctenyl, but also tetrahydropyranyl, dioxanyl, dioxolanyl, morpholinyl, piperidinyl, piperazinyl, pyrazolinonyl and pyrrolidinyl.

The term "$(CH_2)_{3-6}$" denotes —CH$_2$—CH$_2$—CH$_2$—, —CH$_2$—CH$_2$—CH$_2$—CH$_2$—, —CH$_2$—CH$_2$—CH$_2$—CH$_2$—CH$_2$— und CH$_2$—CH$_2$—CH$_2$—CH$_2$—CH$_2$—CH$_2$—.

The term "aryl", according to this invention, denotes carbocyclic ring systems comprising at least one aromatic ring, but without a heteroatom in only one of the rings, inter alia phenyls, naphthyls and phenanthrenyls, fluoranthenyls, fluorenyls, indanyls and tetralinyls. The aryl radicals can also be condensed with further saturated, (partially) unsaturated or aromatic ring systems. Each aryl radical can be present unsubstituted or singly or multiply substituted, wherein the aryl substituents may be the same or different and in any desired and possible position of the aryl. Phenyl or naphthyl radicals are particularly advantageous.

The term "heteroaryl" represents a 5-, 6- or 7-membered cyclic aromatic radical, which contains at least 1 heteroatom, optionally also 2, 3, 4 or 5 heteroatoms, wherein the heteroatoms may be the same or different and the heterocycle may be unsubstituted or singly or multiply substituted; in the case of substitution on the heterocycle, the substituents may be the same or different and in any desired and possible position of the heteroaryl. The heterocycle may also be part of a bi- or polycyclic system. Preferred heteroatoms are nitrogen, oxygen and sulphur. It is preferred for the heteroaryl radical to be selected from the group comprising pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, phthalazinyl, pyrazolyl, imidazolyl, thiazolyl, oxazolyl, isoxazoyl, pyrrolyl, isoxazoyl, pyridinyl, pyridazinyl, pyrimidinyl, pyrazinyl, pyranyl, indazolyl, purinyl, indolizinyl, quinolinyl, isoquinolinyl, isothiazolyl, imidazolyl, triazolyl, triazinyl, quinazolinyl, carbazolyl, phenazinyl, phenothiazinyl or oxadiazolyl, wherein the binding with the compounds of general structure I can be made via any desired and possible ring member of the heteroaryl radical.

In conjunction with "alkyl", the term "substituted", according to this invention, denotes substitution of one or more hydrogen radicals by F, Cl, Br, I, —CN, ═O, ═S, NH$_2$, NH-alkyl, NH-aryl, NH-heteroaryl, NH-cycloalkyl, NH-alkyl-aryl, NH-alkyl-heteroaryl, NH-alkyl-OH, N(alkyl)$_2$, N(alkyl-aryl)$_2$, N(alkyl-heteroaryl)$_2$, N(cycloalkyl)$_2$, N(alkyl-OH)$_2$, NH(C═O)alkyl, NH(C═O)aryl, NO$_2$, SH, S-alkyl, S-aryl, S-heteroaryl, S-alkyl-aryl, S-alkyl-heteroaryl, S-cycloalkyl, S-alkyl-OH, S-alkyl-SH, OH, O-alkyl, O-aryl, O-heteroaryl, O-alkyl-aryl, O-alkyl-heteroaryl, O-cycloalkyl, O-alkyl-OH, CHO, C(═O)$C_{1-6}$ alkyl, C(═S)$C_{1-6}$ alkyl, C(═O)aryl, C(═S)aryl, C(═O)$C_{1-6}$ alkyl-aryl, C(═S)$C_{1-6}$-alkyl aryl, C(═O)-heteroaryl, C(═S)-heteroaryl, C(═O)-cycloalkyl, C(═S)-cycloalkyl, CO$_2$H, CO$_2$-alkyl, CO$_2$-alkyl-aryl, C(═O)NH$_2$, C(═O)NH-alkyl, C(═O)NH-aryl, C(═O)NH-cycloalkyl, C(═O)N(alkyl)$_2$, C(═O)N(alkyl-aryl)$_2$, C(═O)N(alkyl-heteroaryl)$_2$, C(═O)N(cycloalkyl)$_2$, SO-alkyl, SO$_2$-alkyl, SO$_2$NH$_2$, SO$_3$H, PO(O—$C_{1-6}$ alkyl)$_2$, cycloalkyl, aryl or heteroaryl, wherein the term "multiply substituted radicals" denotes radicals that have been multiply substituted, for example twice or three times, either on different or on the same atoms, for example three times on the same C atom, as in the case of CF$_3$ or —CH$_2$CF$_3$, or in various positions, as in the case of —CH(OH)—CH═CH—CHCl$_2$. Multiple substitution can take place with the same substituent or with different substituents. A substituent may optionally also be substituted for its part; thus —O-alkyl also includes inter alia —O—CH$_2$—CH$_2$—O—CH$_2$—CH$_2$—OH.

With respect to "aryl", "heteroaryl" and "cycloalkyl", according to this invention, "singly or multiply substituted" denotes the single or multiple, for example double, treble, quadruple or quintuple, substitution of one or more hydrogen atoms of the ring system by F, Cl, Br, I, CN, NH$_2$, NH-alkyl, NH-aryl, NH-heteroaryl, NH-alkyl-aryl, NH-alkyl-heteroaryl, NH-cycloalkyl, NH-alkyl-OH, N(alkyl)$_2$, N(alkyl-aryl)$_2$, N(alkyl-heteroaryl)$_2$, N(cycloalkyl)$_2$, N(alkyl-OH)$_2$, NO$_2$, SH, S-alkyl, S-cycloalkyl, S-aryl, S-heteroaryl, S-alkyl-aryl, S-alkyl-heteroaryl, S-cycloalkyl, S-alkyl-OH, S-alkyl-SH, OH, O-alkyl, O-cycloalkyl, O-aryl, O-heteroaryl, O-alkyl-aryl, O-alkyl-heteroaryl, O-cycloalkyl, O-alkyl-OH, CHO, C(═O)$C_{1-6}$ alkyl, C(═S)$C_{1-6}$ alkyl, C(═O)aryl, C(=S)aryl, C(=O)—$C_{1-6}$ alkyl-aryl, C(=S)$C_{1-6}$ alkyl-aryl, C(=O)-heteroaryl, C(=S)-heteroaryl, C(=O)-cycloalkyl, C(=S)-cycloalkyl, $CO_2H$, $CO_2$-alkyl, $CO_2$-alkyl-aryl, C(=O)$NH_2$, C(=O)NH-alkyl, C(=O)NH-aryl, C(=O)NH-cycloalkyl, C(=O)N(alkyl)$_2$, C(=O)N(alkyl-aryl)$_2$, C(=O)N(alkyl-heteroaryl)$_2$, C(=O)N(cycloalkyl)$_2$, S(O)-alkyl, S(O)-aryl, $SO_2$-alkyl, $SO_2$-aryl, $SO_2NH_2$, $SO_3H$, $CF_3$, =O, =S;

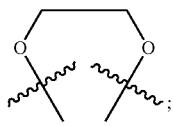

alkyl, cycloalkyl, aryl and/or heteroaryl; on one atom or optionally on different atoms (wherein a substituent can, in turn, optionally be substituted). Multiple substitution takes place here using the same or different substituents.

The term "salt" denotes any form of the active ingredient according to this invention in which it assumes or is charged with an ionic form and is coupled to a counter ion (a cation or anion) or is in solution. This also includes complexes of the active ingredient with other molecules and ions, in particular complexes complexed by ionic interactions. In particular this denotes (and this is also a preferred embodiment of this invention) physiologically acceptable salts, in particular physiologically acceptable salts with cations or bases and physiologically acceptable salts with anions or acids or else a salt formed with a physiologically acceptable acid or physiologically acceptable cation.

The term "physiologically acceptable salt with anions or acids" denotes, in the context of this invention, salts of at least one of the compounds according to this invention—usually protonated, for example on nitrogen—as a cation with at least one anion which are physiologically acceptable—in particular when applied to humans and/or mammals. In the context of this invention this denotes, in particular, the salt formed with a physiologically acceptable acid, namely salts of the respective active ingredient with inorganic or organic acids which are physiologically acceptable—in particular when applied to humans and/or mammals. Examples of physiologically acceptable salts of specific acids include salts of: hydrochloric acid, hydrobromic acid, sulphuric acid, methane sulphonic acid, formic acid, acetic acid, oxalic acid, succinic acid, malic acid, tartaric acid, mandelic acid, fumaric acid, lactic acid, citric acid, glutamic acid, saccharic acid, monomethyl sebacic acid, 5-oxo-proline, hexane-1-sulphonic acid, nicotinic acid, 2-, 3- or 4-amino benzoic acid, 2,4,6-trimethyl-benzoic acid, α-lipoic acid, acetyl glycine, phosphoric acid, maleic acid, malonic acid, hippuric acid and/or aspartic acid. The hydrochloride salt, the citrate and the hemicitrate are particularly preferred.

The term "salt formed with a physiologically acceptable acid", according to this invention, denotes salts of the respective active ingredient with inorganic or organic acids which are physiologically acceptable—in particular when applied to humans and/or mammals. The hydrochloride and the citrate are particularly preferred. Examples of physiologically acceptable acids include: hydrochloric acid, hydrobromic acid, sulphuric acid, methane sulphonic acid, formic acid, acetic acid, oxalic acid, succinic acid, tartaric acid, mandelic acid, fumaric acid, lactic acid, citric acid, glutamic acid, saccharic acid, monomethyl sebacic acid, 5-oxo-proline, hexane-1-sulphonic acid, nicotinic acid, 2-, 3- or 4-amino benzoic acid, 2,4,6-trimethyl-benzoic acid, α-lipoic acid, acetyl glycine, hippuric acid and/or aspartic acid.

The term "physiologically acceptable salt with cations or bases" denotes, in the context of this invention, salts of at least one of the compounds according to this invention—usually a (deprotonated) acid—as an anion with at least one, preferably inorganic, cation, which are physiologically acceptable, in particular when applied to humans and/or mammals. The salts of the alkali and alkaline-earth metals are particularly preferred, but also ammonium salts, in particular (mono-) or (di-) sodium, (mono-) or (di-)potassium, magnesium or calcium salts.

The term "salt formed with a physiologically acceptable cation" denotes, according to this invention, salts of at least one of the respective compounds as an anion with at least one inorganic cation, which are physiologically acceptable, in particular when applied to humans and/or mammals. The salts of the alkali and alkaline-earth metals are particularly preferred, but also ammonium salts, in particular (mono-) or (di-)sodium, (mono-) or (di-)potassium, magnesium or calcium salts.

For a preferred embodiment of the substituted cyclohexyl-1,4-diamine derivatives according to the invention.

$R^1$ and $R^2$ independently of one another represent H; saturated or unsaturated, branched or unbranched, singly or multiply substituted or unsubstituted $C_{1-5}$ alkyl;

or the radicals $R^1$ and $R^2$ together form a ring and represent $CH_2CH_2OCH_2CH_2$, $CH_2CH_2NR^{10}CH_2CH_2$ or $(CH_2)_{3-6}$, wherein $R^{10}$ represents H; saturated or unsaturated, branched or unbranched, singly or multiply substituted or unsubstituted $C_{1-5}$ alkyl.

Particularly preferred are substituted cyclohexyl-1,4-diamine derivatives, wherein $R^1$ and $R^2$ independently of one another represent $CH_3$ or H, wherein $R^1$ and $R^2$ do not simultaneously represent H, or $R^1$ and $R^2$ represent $CH_2CH_2OCH_2$ Also preferred are substituted cyclohexyl-1,4-diamine derivatives, wherein $R^3$ represents respectively unsubstituted or singly or multiply substituted cyclopentyl, cyclohexyl, phenyl, benzyl, naphthyl, anthracenyl, thiophenyl, benzothiophenyl, furyl, benzofuranyl, benzodioxolanyl, indolyl, indanyl, benzodioxanyl, pyrrolyl, pyridyl, pyrimidyl or pyrazinyl; respectively unsubstituted or singly or multiply substituted $C_{5-6}$ cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl bound by a saturated, unbranched $C_{1-2}$ alkyl group;

in particular $R^3$ represents respectively unsubstituted or singly or multiply substituted phenyl, furyl, thiophenyl, naphthyl, benzyl, benzofuranyl, indolyl, indanyl, benzodioxanyl, benzodioxanyl, pyridyl, pyrimidyl, pyrazinyl or benzothiophenyl; respectively unsubstituted or singly or multiply substituted phenyl, furyl or thiophenyl bound by a saturated, unbranched $C_{1-2}$ alkyl group.

Particularly preferred are substituted cyclohexyl-1,4-diamine derivatives, wherein $R^3$ represents respectively substituted or unsubstituted phenyl, phenethyl, thiophenyl, pyridyl or benzyl, particularly preferably phenyl, thienyl, 4-chlorobenzyl, benzyl, 3-chloro-benzyl, 4-methylbenzyl, 2-chlorobenzyl, 4-fluoro-benzyl, 3-methylbenzyl, 2-methylbenzyl, 3-fluoro-benzyl, 2-fluoro-benzyl or phenethyl.

Also preferred are substituted cyclohexyl-1,4-diamine derivatives, wherein $R^4$ represents respectively unsubstituted or singly or multiply substituted $C_{1-5}$ alkyl, cyclohexyl, cyclopentyl, cyclobutyl, cycloheptyl, cyclooctyl, phenyl, benzyl, naphthyl, anthracenyl, thiophenyl, benzothiophenyl, furanyl, isothiazolyl, imidazolyl, triazolyl, triazinyl, pyrazolinonyl, benzofuranyl, benzodioxolanyl, isoquinolinyl, phthalazine, benzo[1,2,5]thiadiazole, benzothiazole, benzotriazole, quinolinyl, carbazole, isoxazolyl, oxazolyl, indolyl, indanyl, benzodioxanyl, indazolyl, benzimidazolyl, pyrrolyl, pyridyl, pyrimidyl or pyrazinyl; respectively unsubstituted or singly or multiply substituted phenyl, naphthyl, anthracenyl, thiophenyl, benzothiophenyl, pyridyl, furyl, benzofuranyl, indolyl, indanyl, benzodioxanyl, pyrrolyl, pyrimidyl or pyrazinyl bound by a saturated, unbranched $C_{1-2}$ alkyl group, in particular $R^4$ represents respectively unsubstituted or singly or multiply substituted $C_{1-5}$ alkyl, cyclohexyl, phenyl, benzyl, naphthyl, thiophenyl, benzothiophenyl, furanyl, isothiazolyl, imidazolyl, triazolyl, pyrazolyl, benzofuranyl, isoquinolinyl, benzothiazole, benzotriazole, quinolinyl, isoxazolyl, oxazolyl, indolyl, pyrrolyl, pyridyl, pyrimidyl or pyrazinyl; respectively unsubstituted or singly or multiply substituted benzyl or phenethyl.

Particularly preferred are substituted cyclohexyl-1,4-diamine derivatives, wherein $R^4$ represents respectively unsubstituted or singly or multiply substituted phenyl, indolyl or methyl.

Also preferred are substituted cyclohexyl-1,4-diamine derivatives wherein X represents branched or unbranched, unsubstituted or singly or multiply substituted $C_{1-5}$ alkyl or an unsubstituted or singly or multiply substituted phenyl or $C_{3-8}$ cycloalkyl radical bound by a branched or unbranched, substituted or unsubstituted $C_{1-3}$ alkyl chain.

Also preferred are substituted cyclohexyl-1,4-diamine derivatives, wherein n represents 0.

Most preferred are substituted cyclohexyl-1,4-diamine derivatives from the group comprising 5-oxo-5-phenyl-valeric acid 4-dimethylamino-4-phenyl-cyclohexyl)-amide N-(4-dimethylamino-4-thiophen-2-yl-cyclohexyl)-4-(4-fluoro-phenyl)-4-oxo-butyramide 2-(3-benzofuryl-phenyl)-N-(4-dimethylamino-4-phenethyl-cyclohexyl)-propionamide 5-oxo-5-phenyl-pentanoic acid (4-dimethylamino-4-phenethyl-cyclohexyl)-amide 2-(3-benzoyl-phenyl)-N-[4-dimethylamino-4-(2-fluoro-benzyl)-cyclohexyl]-propionamide 5-oxo-5-phenyl-valeric acid [4-dimethylamino-4-(2-fluoro-benzyl)-cyclohexyl]-amide 2-(3-benzoyl-phenyl)-N-(4-benzyl-4-dimethylamino-cyclohexyl)-propionamide N-[4-dimethylamino-4-(3-fluoro-phenyl)-cyclohexyl]-2-(1H-indol-3-yl)-2-oxo-acetamide 2-(3-acetyl-2,2-dimethylamino-cyclobutyl)-N-[4-dimethylamino-4-(2-fluoro-benzyl)-cyclohexyl]-acetamide 2-(3-benzoyl-phenyl)-N-[4-dimethylamino-4-(3-methyl-benzyl)-cyclohexyl]-propionamide 2-(3-benzoyl-phenyl)-N-[4-dimethylamino-4-(2-methyl-benzyl)-cyclohexyl]-propionamide N-[4-(2-chloro-benzyl)-4-dimethylamino-cyclohexyl]-4-(4-chloro-phenyl)-4-oxo-butyramide 4-oxo-4-phenyl-(4-phenyl-4-piperidin-1-yl-cyclohexyl)-butyramide 2-(3-acetyl-2,2-dimethylamino-cyclobutyl)-N-[4-dimethylamino -4-(3-methyl-benzyl)-cyclohexyl]-acetamide 4-(4-fluoro-phenyl)-4-oxo-N-(4-phenyl-4-piperidin-1-yl-cyclohexyl)-butyramide 2-(3-benzoyl-phenyl)-N-[4-(3-chloro-benzyl)-4-dimethylamino-cyclohexyl]-propionamide 5-oxo-5-phenyl-valeric acid [4-(3-chloro-benzyl)-4-dimethylamino-cyclohexyl]-amide N-[4-dimethylamino-4-(2-fluoro-benzyl)-cyclohexyl]-4-(4-fluoro-phenyl)-4-oxo-butyramide 2-(3-benzoyl-phenyl)-N-[4-dimethylamino-4-(4-methyl-benzyl)-cyclohexyl]-propionamide N-(4-dimethylamino-4-phenethyl-cyclohexyl)-4-oxo-4-phenyl-butyramide N-[4-dimethylamino-4-(2-methyl-benzyl)-cyclohexyl]-4-oxo-4-phenyl-butyramide N-[4-dimethylamino-4-(3-methyl-benzyl)-cyclohexyl]-4-oxo-4-phenyl-butyramide N-[4-(2-chloro-benzyl)-4-dimethylamino-cyclohexyl]-4-oxo-4-phenyl-butyramide 5-oxo-5-phenyl-valeric acid (4-phenyl-4-piperidin-1-yl-cyclohexyl)-amide 2-(3-acetyl-2,2-dimethyl-cyclobutyl)-N-[4-dimethylamino-4-(4-methyl-benzyl)-cyclohexyl]-acetamide N-(4-benzyl-4-dimethylamino-cyclohexyl)-4-(4-fluoro-phenyl)-4-oxo-butyramide N-[4-dimethylamino-4-(2-fluoro-benzyl)-cyclohexyl]-2-(1H-indol-3-yl)-2-oxo-acetamide 5-oxo-5-phenyl-valeric acid [4-dimethylamino-4-(4-methyl-benzyl)-cyclohexyl]-amide 4-(4-chloro-phenyl)-4-dimethylamino-4-(4-fluoro-benzyl)-cyclohexyl]-4-oxo-butyramide 2-(3-acetyl-2,2-dimethylamino-cyclobutyl)-N-[4-(4-chloro-benzyl)-4-dimethylamino-cyclohexyl]-acetamide N-(4-dimethylamino-4-phenethyl-cyclohexyl)-2-(1H-indol-3-yl)-2-oxo-acetamide 2-(3-acetyl-2,2-dimethyl-cyclobutyl)-N-[4-(3-chloro-benzyl)-4-dimethylamino-cyclohexyl]-acetamide N-[4-dimethylamino-4-(4-fluoro-benzyl)-cyclohexyl]-4-oxo-4-phenyl-butyramide N-[4-(3-chloro-benzyl)-4-dimethylamino-cyclohexyl]-4-(4-fluoro-phenyl)-4-oxo-butyramide 2-(3-acetyl-2,2-dimethylamino-cyclobutyl)-N-(4-benzyl-4-piperidin-1-yl-cyclohexyl)-acetamide 4-(4-chloro-phenyl)-N-[4-dimethylamino-4-(2-methyl-benzyl)-cyclohexyl-4-oxobutyramide N-[4-dimethylamino-4-(4-methyl-benzyl)-cyclohexyl]-4-oxo-4-phenyl-butyramide N-(4-benzyl-4-dimethylamino-cyclohexyl)-4-(4-chloro-phenyl)-4-oxo-butyramide 5-oxo-5-phenyl-valeric acid [4-(4-chloro-benzyl)-4-dimethylamino-cyclohexyl]-amide 4-(4-chloro-phenyl)-N-[4-dimethylamino-4-(4-methyl-benzyl)-cyclohexyl]-4-oxo-butyramide N-[4-dimethylamino-4-(3-fluoro-benzyl)-cyclohexyl]-4-(4-fluoro-phenyl)-4-oxo-butyramide 4-(4-chloro-phenyl)-4-dimethylamino-4-(3-fluoro-benzyl)-cyclohexyl]-4-oxo-butyramide 2-(3-acetyl-2,2-dimethylamino-cyclobutyl)-N-(4-benzyl-4-dimethylamino-cyclohexyl)-acetamide 5-oxo-5-phenyl-valeric acid (4-morpholin-4-yl-4-phenyl-cyclohexyl)-amide N-[4-dimethylamino-4-(2-methyl-benzyl)-cyclohexyl]-2-(1H-indol-3-yl)-2-oxo-acetamide N-[4-dimethylamino-4-(3-methyl-benzyl)-cyclohexyl]-2-(1H-indol-3-yl)-2-oxo-acetamide N-[4-dimethylamino-4-(4-fluoro-benzyl)-cyclohexyl]-2-(1H-indol-3-yl)-2-oxo-acetamide N-[4-(2-chloro-benzyl)-4-dimethylamino-cyclohexyl]-2-(1H-indol-3-yl)-2-oxo-acetamide 7-oxo-octanoic acid (4-benzyl-4-dimethylamino-cyclohexyl)-amide N-[4-(4-chloro-benzyl)-4-dimethylamino-cyclohexyl]-4-(4-fluoro-phenyl)-4-oxo-butyramide 4-(4-chloro-phenyl)-N-(4-morpholinyl-4-yl-4-phenyl-cyclohexyl)-4-oxo-butyramide N-(4-benzyl-4-piperidin-yl-cyclohexyl)-4-oxo-4-phenyl-butyramide N-[4-dimethylamino-4-(4-methyl-benzyl)-cyclohexyl]-4-(4-fluoro-phenyl)-4-oxo-butyramide N-(4-benzyl-4-piperidin-1-yl-cyclohexyl)-4-(4-fluoro-phenyl)-4-oxo-butyramide 7-oxo-octanoic acid [4-dimethylamino-4-(4-methyl-benzyl)-cyclohexyl]-amide 6-oxo-heptanoic acid [4-(3-chloro-benzyl)-4-dimethylamino-cyclohexyl]-amide 2-(3-benzoyl-phenyl)-N-(4-benzyl-4-pyrrolidin-1-yl-cyclohexyl)-propionamide 2-(3-benzoyl-phenyl)-N-(4-phenyl-4-piperidin-1-yl-cyclohexyl)-propionamide 6-oxo-heptanoic acid [4-(4-chloro-benzyl)-4-dimethylamino-cyclohexyl]-amide 6-oxo-heptanoic acid (4-morpholin-4-yl-4-phenyl-cyclohexyl)-amide 4-(4-chloro-phenyl)-N-(4-dimethylamino-4-phenylcyclohexyl)-4-oxobutyramide hydrochloride, non-polar diastereoisomer 4-(4-chloro-phenyl)-N-(4-dimethylamino-4-phenylcyclohexyl)-4-oxobutyramide hydrochloride, polar diastereoisomer 5-oxo-5-phenylpentanoic acid (4-dimethylamino-4-phenyl-cyclohexyl)amide hydrochloride, non-polar diastereoisomer 5-oxo-5-phenylpentanoic acid (4-dimethylamino-4-phenyl-cyclohexyl)amide hydrochloride, polar diastereoisomer in the form of the racemate; the enantiomers, diastereomers, mixtures of the enantiomers or diastereomers or an individual enantiomer or diastereomer; the bases and/or salts of physiologically acceptable acids or cations.

The substances according to the invention act, for example, on the μ-opioid receptor that is relevant in connection with various diseases, so they are suitable as a pharmaceutical active ingredient in a pharmaceutical composition. The invention therefore also relates to pharmaceutical compositions containing at least one substituted cyclohexyl-1,4-diamine derivative according to the invention, and optionally suitable additives and/or auxiliaries and/or optionally further active ingredients.

The pharmaceutical preparations according to the invention contain, in addition to at least one substituted cyclohexyl-1,4-diamine derivative according to the invention, optionally suitable additives and/or auxiliaries, therefore also excipients, fillers, solvents, diluents, dyes and/or binders and can be administered as liquid pharmaceutical preparations in the form of injection solutions, drops or syrups, as semi-solid pharmaceutical preparations in the form of granules, tablets, pellets, patches, capsules, plasters or aerosols. The choice of auxiliaries, etc. and the amounts thereof to be used depend on whether the pharmaceutical preparation is to be applied orally, perorally, parenterally, intravenously, intraperitoneally, intradermally, intramuscularly, intranasally, buccally, rectally or topically, for example to the skin, the mucous membranes or the eyes. Preparations in the form of tablets, dragees, capsules, granules, drops, juices and syrups are suitable for oral application, solutions, suspensions, easily reconstitutable dry preparations and sprays are suitable for parenteral, topical and inhalative applications. Substituted cyclohexyl-1,4-diamine derivatives according to the invention in a deposit, in dissolved form or in a plaster, optionally with the addition of agents to promote skin penetration, are suitable percutaneous application preparations. Orally or percutaneously applicable preparation forms can release the substituted cyclohexyl-1,4-diamine derivatives according to the invention after a delay. The substituted cyclohexyl-1,4-diamine derivatives according to the invention may also be applied in the form of parenteral long-acting repositories such as implants or implanted pumps. In principle, further active ingredients known to the person skilled in the art can be added to the pharmaceutical preparations according to the invention.

The amount of active ingredient to be administered to the patient varies as a function of the weight of the patient, the method of application, the indication and the severity of the illness. Conventionally, 0.00005 to 50 mg/kg, preferably 0.01 to 5 mg/kg, of at least one substituted cyclohexyl-1,4-diamine derivative according to the invention are applied.

For all of the above-mentioned forms of the pharmaceutical composition according to the invention, it is particularly preferred if, in addition to at least one substituted cyclohexyl-1,4-diamine derivative, the pharmaceutical composition contains a further active ingredient, in particular an opioid, preferably a strong opioid, in particular morphine, or an anaesthetic, preferably hexobarbital or halothane.

In a preferred form of the pharmaceutical composition, a contained substituted cyclohexyl-1,4-diamine derivative according to the invention is in the form of a pure diastereomer and/or enantiomer, as a racemate or as a non-equimolar or equimolar blend of the diastereomers and/or enantiomers.

Both the ORL1 receptor and the further opioid receptors have been identified in particular in the occurrence of pain. Accordingly, substituted cyclohexyl-1,4-diamine derivatives according to the invention can be used for producing a pharmaceutical composition for the treatment of pain, in particular acute, neuropathic or chronic pain.

The invention therefore also relates to the use of a substituted cyclohexyl-1,4-diamine derivative according to the invention for producing a pharmaceutical composition for treating pain, in particular acute, visceral, neuropathic or chronic pain.

The invention also relates to the use of a substituted cyclohexyl-1,4-diamine derivative according to the invention for the production of a pharmaceutical composition for the treatment of anxiety, stress and stress-related syndromes, depression, epilepsy, Alzheimer's disease, senile dementia, catalepsy, general cognitive dysfunction, learning and memory disorders (as a nootropic), withdrawal symptoms, alcohol- and/or drug- and/or medicine abuse and/or dependency, sexual dysfunction, cardiovascular diseases, hypotension, hypertension, tinnitus, pruritus, migraine, hearing difficulties, deficient intestinal motility, impaired nutrient absorption, anorexia, obesity, locomotive disorders, diarrhea, cachexia, urinary incontinence, or as a muscle relaxant, anticonvulsive or anaesthetic or for co-administration in treatment with an opioid analgesic or anaesthetic, for diuresis or anti-natriuresis, anxiolysis, for modulation of motor activity, for modulation of neurotransmitter release and treatment of neurodegenerative diseases associated therewith, for the treatment of withdrawal symptoms and/or for reducing opioid addiction potential.

In this case it may be preferred in one of the present uses if a substituted cyclohexyl-1,4-diamine derivative used is present as a pure diastereomer and/or enantiomer, as a racemate or as a non-equimolar or equimolar blend of the diastereomers and/or enantiomers.

The invention also relates to a process for the treatment, in particular in one of the above-mentioned indications, of a non-human mammal or human, which or who requires treatment of pain, in particular chronic pain, by administration of a therapeutically effective dose of a substituted cyclohexyl-1,4-diamine derivative according to the invention, or of a pharmaceutical composition according to the invention.

The invention also relates to a process for producing the substituted cyclohexyl-1,4-diamine derivatives according to the invention, as stated in the following description and examples.

The radicals $R^{01}$ and $R^{02}$ have the meaning given for compounds according to the invention of formula I for $R^1$ and $R^2$ and, in addition, independently of one another can represent a protecting group. The remaining radicals have the meaning indicated in formula I:

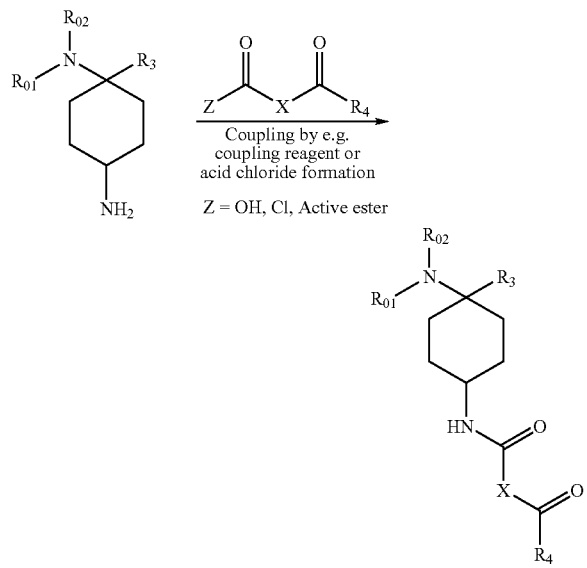

Basically the various methods, known to a person skilled in the art, for producing amides are suitable for providing the substances according to the invention.

The process according to the invention is preferably based on linking substituted cyclohexane-1,4-diamine (WO 02090317) with suitable carboxylic acids and/or carboxylic acid derivatives, in particular carboxylic acid chlorides or bromides, and thus converting them into compounds according to the invention. Polar or non-polar aprotic solvents to which an organic or inorganic auxiliary base, preferably tertiary amines such as triethylamine, diisopropylethylamine or DMAP has been added, are used in reactions with acid chlorides and bromides. In addition to amines of this type pyridine, for example, is also suitable as a base and as a solvent. Preferably, acid chlorides are reacted with amines at −30 bis +40° C. in dichloromethane or chloroform in the presence of triethylamine or pyridine and optionally catalytic amounts of DMAP. The entire range of methods, known to a person skilled in the art, for producing amides is also available for reacting carboxylic acids with a substituted cyclohexane-1, 4-diamine (WO 02090317). The use of organic or inorganic dehydrating agents such as a molecular sieve, magnesium sulphate, sulphuric acid or carbodiimides such as DCC or DIC, DIC optionally in the presence of HOBt, is advantageous. These reactions are also preferably carried out in polar or non-polar aprotic solvents at temperatures between −30 and +110° C., preferably −10 and +40° C. The protecting groups are optionally subsequently cleaved.

EXAMPLES

The following examples serve to describe the invention in more detail, but do not limit the general idea of the invention.

The yields of the compounds produced have not been optimised.

All temperatures are uncorrected.

The term "ether" means diethylether, "EE" ethylacetate and "DCM" dichloromethane. The term "equivalents" means amount of substance equivalents, "mp." melting point or melting range, "decomp." decomposition, "RT" room temperature, "abs." absolute (anhydrous), "rac." racemic, "conc." concentrated, "min" minutes, "h" hours, "d" days, "vol. %" volume percent, "m %" mass percent and "M" is an indication of concentration in mol/l.

Silica gel 60 (0.040-0.063 mm) from E. Merck, Darmstadt was used as the stationary phase for column chromatography.

The thin-layer chromatography tests were carried out using HPTLC chromatoplates, silica gel 60 F 254, from E. Merck, Darmstadt.

The mixing ratios of eluants for chromatography tests are always given in volume/volume.

The compounds used in the following were either commercially available, or production thereof is known from the prior art or has been derived from the prior art in a manner obvious to a person skilled in the art.

General Directions:

0.1 mmol of an acid chloride, which was prepared from the corresponding carboxylic acids by methods known to a person skilled in the art (see Table 1), was added to 0.1 mmol of the cyclohexane-1,4-diamine in the presence of 1.05 equivalents triethylamine. The mixture was stirred for 12 h and a 1M sodium carbonate solution was then added. The product was obtained by extraction with 3×2 ml dichloromethane, in each case, and removal of the solvent.

The carboxylic acids used for the last step of the examples are indicated in Table 1.

TABLE 1

List of examples and diagrams of the carboxylic acids used in the last synthesis step.

| Example | Carboxylic acid used | Name of example compound |
|---|---|---|
| 1 | ![structure] | 5-oxo-5-phenyl-valeric acid 4-dimethylamino-4-phenyl-cyclohexyl)-amide |

TABLE 1-continued

List of examples and diagrams of the carboxylic acids used in the last synthesis step.

| Example | Carboxylic acid used | Name of example compound |
|---|---|---|
| 2 | 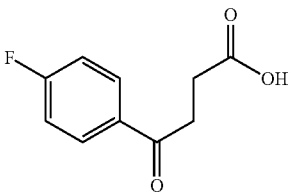 | N-(4-dimethylamino-4-thiophen-2-yl-cyclohexyl)-4-(4-fluoro-phenyl)-4-oxo-butyramide |
| 3 | 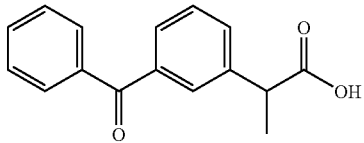 | 2-(3-benzofuryl-phenyl)-N-(4-dimethylamino-4-phenethyl-cyclohexyl)-propionamide |
| 4 | 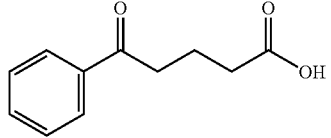 | 5-oxo-5-phenyl-pentanoic acid (4-dimethylamino-4-phenethyl-cyclohexyl)-amide |
| 5 | 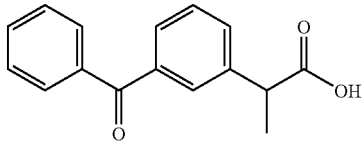 | 2-(3-benzoyl-phenyl)-N-[4-dimethylamino-4-(2-fluoro-benzyl)-cyclohexyl]-propionamide |
| 6 | 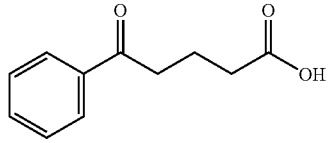 | 5-oxo-5-phenyl-valeric acid [4-dimethylamino-4-(2-fluoro-benzyl)-cyclohexyl]-amide |
| 7 | 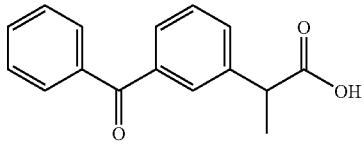 | 2-(3-benzoyl-phenyl)-N-(4-benzyl-4-dimethylamino-cyclohexyl)-propionamide |
| 8 | 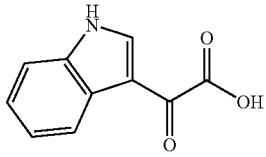 | N-[4-dimethylamino-4-(3-fluoro-phenyl)-cyclohexyl]-2-(1H-indol-3-yl)-2-oxo-acetamide |
| 9 | 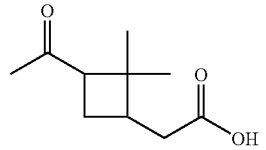 | 2-(3-acetyl-2,2-dimethylamino-cyclobutyl)-N-[4-dimethylamino-4-(2-fluoro-benzyl)-cyclohexyl]-acetamide |
| 10 | 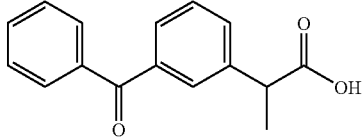 | 2-(3-benzoyl-phenyl)-N-[4-dimethylamino-4-(3-methyl-benzyl)-cyclohexyl]-propionamide |

TABLE 1-continued

List of examples and diagrams of the carboxylic acids used in the last synthesis step.

| Example | Carboxylic acid used | Name of example compound |
|---|---|---|
| 11 | | 2-(3-benzoyl-phenyl)-N-[4-dimethylamino-4-(2-methyl-benzyl)-cyclohexyl]-propionamide |
| 12 | | N-[4-(2-chloro-benzyl)-4-dimethylamino-cyclohexyl]-4-(4-chloro-phenyl)-4-oxo-butyramide |
| 13 | | 4-oxo-4-phenyl-(4-phenyl-4-piperidin-1-yl-cyclohexyl)-butyramide |
| 14 | | 2-(3-acetyl-2,2-dimethylamino-cyclobutyl)-N-[4-dimethylamino-4-(3-methyl-benzyl)-cyclohexyl]-acetamide |
| 15 | | 4-(4-fluoro-phenyl)-4-oxo-N-(4-phenyl-4-piperidin-1-yl-cyclohexyl)-butyramide |
| 16 | | 2-(3-benzoyl-phenyl)-N-[4-(3-chloro-benzyl)-4-dimethylamino-cyclohexyl]-propionamide |
| 17 | | 5-oxo-5-phenyl-valeric acid [4-(3-chloro-benzyl)-4-dimethylamino-cyclohexyl]-amide |
| 18 | | N-[4-dimethylamino-4-(2-fluoro-benzyl)-cyclohexyl]-4-(4-fluoro-phenyl)-4-oxo-butyramide |

TABLE 1-continued

List of examples and diagrams of the carboxylic acids used in the last synthesis step.

| Example | Carboxylic acid used | Name of example compound |
|---|---|---|
| 19 | | 2-(3-benzoyl-phenyl)-N-[4-dimethylamino-4-(4-methyl-benzyl)-cyclohexyl]-propionamide |
| 20 | | N-(4-dimethylamino-4-phenethyl-cyclohexyl)-4-oxo-4-phenyl-butyramide |
| 21 | | N-[4-dimethylamino-4-(2-methyl-benzyl)-cyclohexyl]-4-oxo-4-phenyl-butyramide |
| 22 | | N-[4-dimethylamino-4-(3-methyl-benzyl)-cyclohexyl]-4-oxo-4-phenyl-butyramide |
| 23 | | N-[4-(2-chloro-benzyl)-4-dimethylamino-cyclohexyl]-4-oxo-4-phenyl-butyramide |
| 24 | | 5-oxo-5-phenyl-valeric acid (4-phenyl-4-piperidin-1-yl-cyclohexyl)-amide |
| 25 | | 2-(3-acetyl-2,2-dimethyl-cyclobutyl)-N-[4-dimethylamino-4-(4-methyl-benzyl)-cyclohexyl]-acetamide |
| 26 | | N-(4-benzyl-4-dimethylamino-cyclohexyl)-4-(4-fluoro-phenyl)-4-oxo-butyramide |
| 27 | | N-[4-dimethylamino-4-(2-fluoro-benzyl)-cyclohexyl]-2-(1H-indol-3-yl)-2-oxo-acetamide |

TABLE 1-continued

List of examples and diagrams of the carboxylic acids used in the last synthesis step.

| Example | Carboxylic acid used | Name of example compound |
|---|---|---|
| 28 | | 5-oxo-5-phenyl-valeric acid [4-dimethylamino-4-(4-methyl-benzyl)-cyclohexyl]-amide |
| 29 | | 4-(4-chloro-phenyl)-4-dimethylamino-4-(4-fluoro-benzyl)-cyclohexyl]-4-oxo-butyramide |
| 30 | | 2-(3-acetyl-2,2-dimethyl-cyclobutyl)-N-[4-(4-chloro-benzyl)-4-dimethylamino-cyclohexyl]-acetamide |
| 31 | | N-(4-dimethylamino-4-phenethyl-cyclohexyl)-2-(1H-indol-3-yl)-2-oxo-acetamide |
| 32 | | 2-(3-acetyl-2,2-dimethyl-cyclobutyl)-N-[4-(3-chloro-benzyl)-4-dimethylamino-cyclohexyl]-acetamide |
| 33 | | N-[4-dimethylamino-4-(4-fluoro-benzyl)-cyclohexyl]-4-oxo-4-phenyl-butyramide |
| 34 | | N-[4-(3-chloro-benzyl)-4-dimethylamino-cyclohexyl]-4-(4-fluoro-phenyl)-4-oxo-butyramide |
| 35 | | 2-(3-acetyl-2,2-dimethylamino-cyclobutyl)-N-(4-benzyl-4-piperidin-1-yl-cyclohexyl)-acetamide |

TABLE 1-continued

List of examples and diagrams of the carboxylic acids used in the last synthesis step.

| Example | Carboxylic acid used | Name of example compound |
|---|---|---|
| 36 | | 4-(4-chloro-phenyl)-N-[4-dimethylamino-4-(2-methyl-benzyl)-cyclohexyl-4-oxobutyramide |
| 37 | | N-[4-dimethylamino-4-(4-methyl-benzyl)-cyclohexyl]-4-oxo-4-phenyl-butyramide |
| 38 | | N-(4-benzyl-4-dimethylamino-cyclohexyl)-4-(4-chloro-phenyl)-4-oxo-butyramide |
| 39 | | 5-oxo-5-phenyl-valeric acid [4-(4-chloro-benzyl)-4-dimethylamino-cyclohexyl]-amide |
| 40 | | 4-(4-chloro-phenyl)-N-[4-dimethylamino-4-(4-methyl-benzyl)-cyclohexyl]-4-oxo-butyramide |
| 41 | | N-[4-dimethylamino-4-(3-fluoro-benzyl)-cyclohexyl]-4-(4-fluoro-phenyl)-4-oxo-butyramide |
| 42 | | 4-(4-chloro-phenyl)-4-dimethylamino-4-(3-fluoro-benzyl)-cyclohexyl]-4-oxo-butyramide |
| 43 | | 2-(3-acetyl-2,2-dimethylamino-cyclobutyl)-N-(4-benzyl-4-dimethylamino-cyclohexyl)-acetamide |
| 44 | | 5-oxo-5-phenyl-valeric acid (4-morpholin-4-yl-4-phenyl-cyclohexyl)-amide |

TABLE 1-continued

List of examples and diagrams of the carboxylic acids used in the last synthesis step.

| Example | Carboxylic acid used | Name of example compound |
|---|---|---|
| 45 | 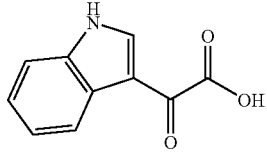 | N-[4-dimethylamino-4-(2-methyl-benzyl)-cyclohexyl]-2-(1H-indol-3-yl)-2-oxo-acetamide |
| 46 | 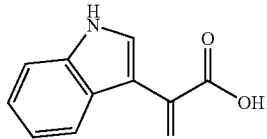 | N-[4-dimethylamino-4-(3-methyl-benzyl)-cyclohexyl]-2-(1H-indol-3-yl)-2-oxo-acetamide |
| 47 | 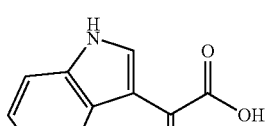 | N-[4-dimethylamino-4-(4-fluoro-benzyl)-cyclohexyl]-2-(1H-indol-3-yl)-2-oxo-acetamide |
| 48 | 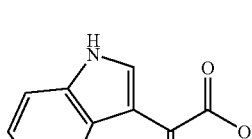 | N-[4-(2-chloro-benzyl)-4-dimethylamino-cyclohexyl]-2-(1H-indol-3-yl)-2-oxo-acetamide |
| 49 | 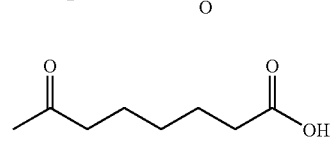 | 7-oxo-octanoic acid (4-benzyl-4-dimethylamino-cyclohexyl)-amide |
| 50 | 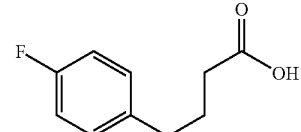 | N-[4-(4-chloro-benzyl)-4-dimethylamino-cyclohexyl]-4-(4-fluoro-phenyl)-4-oxo-butyramide |
| 51 | 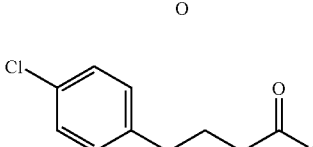 | 4-(4-chloro-phenyl)-N-(4-morpholinyl-4-yl-4-phenyl-cyclohexyl)-4-oxo-butyramide |
| 52 | 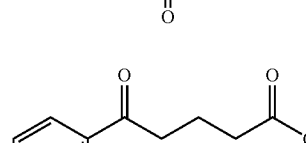 | N-(4-benzyl-4-piperidin-yl-cyclohexyl)-4-oxo-4-phenyl-butyramide |

TABLE 1-continued

List of examples and diagrams of the carboxylic acids used in the last synthesis step.

| Example | Carboxylic acid used | Name of example compound |
|---|---|---|
| 53 | 4-fluorophenyl-CH2-CH2-C(=O)-...-C(=O)-OH | N-[4-dimethylamino-4-(4-methyl-benzyl)-cyclohexyl]-4-(4-fluoro-phenyl)-4-oxo-butyramide |
| 54 | 4-fluorophenyl-CH2-CH2-C(=O)-...-C(=O)-OH | N-(4-benzyl-4-piperidin-1-yl-cyclohexyl)-4-(4-fluoro-phenyl)-4-oxo-butyramide |
| 55 | 7-oxo-octanoic acid | 7-oxo-octanoic acid [4-dimethylamino-4-(4-methyl-benzyl)-cyclohexyl]-amide |
| 56 | 6-oxo-heptanoic acid | 6-oxo-heptanoic acid [4-(3-chloro-benzyl)-4-dimethylamino-cyclohexyl]-amide |
| 57 | 2-(3-benzoyl-phenyl)-propionic acid | 2-(3-benzoyl-phenyl)-N-(4-benzyl-4-pyrrolidin-1-yl-cyclohexyl)-propionamide |
| 58 | 2-(3-benzoyl-phenyl)-propionic acid | 2-(3-benzoyl-phenyl)-N-(4-phenyl-4-piperidin-1-yl-cyclohexyl)-propionamide |
| 59 | 6-oxo-heptanoic acid | 6-oxo-heptanoic acid [4-(4-chloro-benzyl)-4-dimethylamino-cyclohexyl]-amide |
| 60 | 6-oxo-heptanoic acid | 6-oxo-heptanoic acid (4-morpholin-4-yl-4-phenyl-cyclohexyl)-amide |

Example 61

4-(4-chloro-phenyl)-N-(4-dimethylamino-4-phenyl-cyclohexyl)-4-oxobutyramide hydrochloride, non-polar diastereoisomer 310 mg 3-(4-chlorobenzoyl) propanoic acid (4-(4-chloro-phenyl)-4-oxobutyric acid, 1 mol equivalent) dissolved in 1.6 ml DMF (5 mol equivalents) were added to 350 mg of the non-polar diastereoisomer of N,N-dimethyl-1-phenylcyclohexane-1,4-diamine, 230 Al N,N-diisopropylcarbodiimide (DIC, 1 mol equivalent) and 200 μg 1-hydroxybenzotriazole (HOBt, 1 mol equivalent) at 0° C. and while stirring. After three hours at this temperature, the mixture was stirred overnight while heating to room temperature. For working up, one-molar sodium carbonate solution was added (pH >10)

and the crude product (855 mg) isolated by extraction with ethylacetate/THF (V:V=1:1), subsequent drying over sodium sulphate and evaporation. The main fraction of 447 mg obtained by column chromatography on silica gel (4.0×18 cm) with methanol/ethylacetate/n-hexane (V:V:V=1:1:1) was dissolved in 45 ml ethylacetate and was converted into the corresponding hydrochloride of the non-polar diastereoisomer of 4-(4-chloro-phenyl)-N-(4-dimethylamino-4-phenylcyclohexyl)-4-oxobutyramide) by adding 20 μl water and 140 μl chlorotrimethylsilane (353 mg white solid, mp. 177-180° C.).

Example 62

4-(4-chloro-phenyl)-N-(4-dimethylamino-4-phenyl-cyclohexyl)-4-oxobutyramide hydrochloride, polar diastereoisomer As described for Example 61, 310 mg 3-(4-chlorobenzoyl) propanoic acid dissolved in 1.6 ml DMF were added to 350 mg of the polar diastereoisomer of N,N-dimethyl-1-phenyl-cyclohexane-1,4-diamine, 230 [L N,N-diisopropylcarbodiimide and 200 μg 1-hydroxybenzotriazole (HOBt) at 0° C. and while stirring. After three hours at this temperature, the mixture was stirred overnight while heating to room temperature. For working up, one-molar sodium carbonate solution was added (pH>10) and the crude product (1.193 mg) was isolated by extraction with ethylacetate/THF (V:V=1:1), subsequent drying over sodium sulphate and evaporation. The main fraction of 413 mg obtained by column chromatography on silica gel (4.0×18 cm) with methanol/ethylacetate/n-hexane (V:V:V=1:1:1) was dissolved in 41 ml ethylacetate and was converted into the corresponding hydrochloride of the polar diastereoisomer of 4-(4-chloro-phenyl)-N-(4-dimethylamino-4-phenylcyclohexyl)-4-oxobutyramide by adding 18 μl water and 130 μl chlorotrimethylsilane (321 mg white solid).

Example 63

5-oxo-5-phenyl pentanoic acid (4-dimethylamino-4-phenylcyclohexyl)amide hydrochloride, non-polar diastereoisomer 280 mg 4-benzoylbutyric acid (5-oxo-5-phenyl pentanoic acid) dissolved in 1.4 ml DMF were added to 350 mg of the non-polar diastereoisomer of N,N-dimethyl-1-phenylcyclohexane-1,4-diamine, 230 μl N,N-diisopropylcarbodiimide and 200 μg 1-hydroxybenzotriazole (HOBt) at about 5° C. while stirring. After three hours at this temperature, the mixture was stirred overnight while heating to room temperature. For working up, one-molar sodium carbonate solution was added (pH>10) and the crude product (674 mg) isolated by extraction with ethylacetate, subsequent drying over sodium sulphate and evaporation. The main fraction of 295 mg obtained by column chromatography on silica gel (4.0×18 cm) with methanol/ethylacetate/n-hexane (V:V:V=1:1:1) was dissolved in 135 ml ethylacetate and was converted into the corresponding hydrochloride of the non-polar diastereoisomer of 5-oxo-5-phenyl pentanoic acid (4-dimethylamino-4-phenylcyclohexyl)amide by adding 12 μl water and 90 μl chlorotrimethylsilane (310 mg white solid, mp. 127-137° C.).

Example 64

5-oxo-5-phenyl pentanoic acid (4-dimethylamino-4-phenylcyclohexyl)amide hydrochloride, polar diastereoisomer As described for Example 63, 280 mg 5-oxo-5-phenylpentanoylchloride dissolved in 1.6 ml DMF were added to 350 mg of the polar diastereoisomer of N,N-dimethylamino-1-phenylcyclohexane-1,4-diamine, 230 μl N,N-diisopropylcarbodiimide and 200 μg 1-hydroxybenzotriazole (HOBt) at 5° C. while stirring. After three hours at this temperature, the mixture was stirred overnight while heating to room temperature. For working up, one-molar sodium carbonate solution was added (pH>10) and the crude product (794 mg) isolated by extraction with ethylacetate, subsequent drying over sodium sulphate and evaporation. The main fraction of 410 mg obtained by column chromatography on silica gel (4.0×18 cm) with methanol/ethylacetate/n-hexane (V:V:V=1:1:1) was dissolved in 41 ml ethylacetate and was converted into the corresponding hydrochloride of the polar diastereoisomer of 5-oxo-5-phenylpentanoic acid (4-dimethylamino-4-phenylcyclohexyl)amide by adding 19 μl water and 130 μl chlorotrimethylsilane (322 mg white solid).

Tests on the Efficacy of the Compounds According to the Invention:

Measurement of ORL1 Binding

The cyclohexane derivatives of general formula I were examined in a receptor binding assay with 3H-nociceptin/orphanin FQ with membranes of recombinant CHO-ORL1 cells. This test system was carried out according to the methods presented by Ardati et al (Mol. Pharmacol., 51, 1997, pp. 816-824). The concentration of 3H-nociceptin/orphanin FQ was 0.5 nM in these tests. The binding assays were carried out with 20 μg membrane protein per 200 μl batch in 50 mM Hepes, pH 7.4, 10 mM MgCl2 and 1 mM EDTA. The binding with the ORL1 receptor was determined by using 1 mg WGA-SPA beads (Amersham-Pharmacia, Freiburg), by incubation of the batch for one hour at RT and subsequent measurement in the Trilux scintillation counter (Wallac, Finland). The affinity is shown in Table 1 as a nanomolar Ki value in or % inhibition at c=1 μM.

Measurement of μ-binding

The receptor affinity for human μ-opiate receptor was determined in a homogenous batch in microtitre plates. For this purpose, dilution series of the respective substituted cyclohexyl-1,4-diamine derivative to be tested were incubated with a receptor membrane preparation (15-40 μg protein per 250 μl incubation batch) of CHO-K1 cells, which express the human μ-opiate receptor (RB-HOM receptor membrane preparation from NEN, Zaventem, Belgium) in the presence of 1 nmol/l of the radioactive ligand [$^3$H]-naloxone (NET719, NEN, Zaventem, Belgium) and 1 mg WGA-SPA beads (wheat germ agglutinin SPA beads from Amersham/Pharmacia, Freiburg, Germany) in a total volume of 250 μl for 90 minutes at room temperature. 50 mmol/l tris-HCl were added as an incubation buffer with 0.05% by weight sodium azide and 0.06% by weight bovine serum albumin. 25 μmol/l naloxone were also added to determine the non-specific binding. At the end of the 90-minute incubation period, the microtitre plates were centrifuged off for 20 minutes at 1000 g and the radioactivity measured in a β-counter (Microbeta-Trilux, PerkinElmer Wallac, Freiburg, Germany). The percentage displacement of the radioactive ligand from its binding with the human μ-opiate receptor at a concentration of the test substances of 1 μmol/l was determined and given as a percentage inhibition (% inhibition) of the specific binding. $IC_{50}$ inhibition concentrations, which bring about a 50% displacement of the radioactive ligand, were partially calculated by taking as a basis the percentage displacement by various concentrations of the compounds of general formula I to be tested. Ki values for the test substances were obtained as a result of conversion by means of the Cheng-Prusoff equation.

Measurement of Serotonin Re-uptake

In order to carry out these in vitro studies, synaptosomes were freshly isolated from rat brain areas. In each case, what is known as a "P2" fraction, which was prepared in accordance with Gray and Whittaker's directions (E. G. Gray and V. P. Whittaker (1962) J. Anat. 76, 79-88), was used. For the 5HT-uptake, these vesicular particles were isolated from the medulla+pons region of male rat brains.

A detailed description of the method can be found in the literature (M. Ch. Frink, H.-H. Hennies, W. Englberger, M. Haurand and B. Wilffert (1996) Arzneim.-Forsch./Drug Res. 46 (III), 11, 1029-1036).

Measurement of Noradrenalin Re-uptake

In order to carry out these in vitro studies, synaptosomes were freshly isolated from rat brain areas. In each case, what is known as a "$P_2$" fraction, which was prepared in accordance with the directions of Gray and Whittaker (E. G. Gray and V. P. Whittaker (1962) J. Anat. 76, 79-88), was used. For the NA-uptake, these vesicular particles were isolated from the hypothalamus of male rat brains.

A detailed description of the method can be found in the literature (M. Ch. Frink, H.-H. Hennies, W. Englberger, M. Haurand and B. Wilffert (1996) Arzneim.-Forsch./Drug Res. 46 (III), 11, 1029-1036).

The following binding data was determined, by way of example:

| Example | μ-binding [1 μM], % inhibition |
| --- | --- |
| 1 | 100 |
| 2 | 100 |
| 3 | 91 |
| 4 | 88 |
| 5 | 84 |
| 6 | 80 |
| 7 | 80 |
| 8 | 79 |
| 9 | 79 |
| 10 | 79 |
| 11 | 78 |
| 12 | 72 |
| 13 | 71 |
| 14 | 68 |
| 15 | 68 |
| 16 | 68 |
| 17 | 65 |
| 18 | 62 |
| 19 | 62 |
| 20 | 61 |
| 21 | 61 |
| 22 | 60 |
| 23 | 60 |
| 24 | 59 |
| 25 | 58 |
| 26 | 58 |
| 27 | 57 |
| 28 | 56 |
| 29 | 55 |
| 30 | 55 |
| 31 | 55 |
| 32 | 55 |

-continued

| Example | μ-binding [1 μM], % inhibition |
| --- | --- |
| 33 | 54 |
| 34 | 54 |
| 35 | 54 |
| 36 | 53 |
| 37 | 50 |
| 38 | 50 |
| 39 | 48 |
| 40 | 42 |
| 41 | 42 |
| 42 | 42 |
| 43 | 41 |
| 44 | 41 |
| 61 | 92 |
| 62 | 81 |
| 63 | 100 |
| 64 | 89 |

| Example | ORL 1-binding [1 μM], % inhibition |
| --- | --- |
| 1 | 100 |
| 2 | 91 |
| 8 | 78 |
| 61 | 90 |
| 63 | 99 |

| Example | 5HT-uptake [10 μM], % inhibition |
| --- | --- |
| 61 | 78 |
| 62 | 49 |
| 63 | 85 |
| 64 | 62 |

| Example | NA-uptake [10 μM], % inhibition |
| --- | --- |
| 61 | 92 |
| 62 | 55 |
| 63 | 83 |
| 64 | 33 |

Parenteral Solution of a Substituted cyclohexyl-1,4-diamine Derivative According to the Invention 38 g of one of the substituted cyclohexyl-1,4-diamine derivatives according to the invention, here Example 1, was dissolved at room temperature in 1 l water for injection purposes and then adjusted to isotonic conditions for injection purposes by adding anhydrous glucose.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A cyclohexyl-1,4-diamine compound corresponding to formula I,

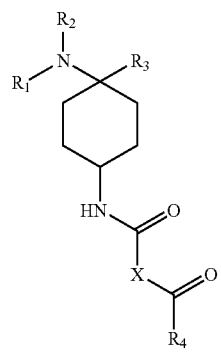

wherein
- $R^1$ and $R^2$ independently of one another represent H; saturated or unsaturated, branched or unbranched, singly or multiply substituted or unsubstituted $C_{1-5}$ alkyl; singly or multiply substituted or unsubstituted $C_{3-8}$ cycloalkyl; or singly or multiply substituted or unsubstituted aryl, $C_{3-8}$ cycloalkyl or heteroaryl bound by $C_{1-3}$ alkyl;
- or $R^1$ and $R^2$ together form a ring and represent $CH_2CH_2OCH_2CH_2$, $CH_2CH_2NR^{10}CH_2CH_2$ or $(CH_2)_{3-6}$,
- wherein $R^{10}$ represents H; saturated or unsaturated, branched or unbranched, singly or multiply substituted or unsubstituted $C_{1-5}$ alkyl; singly or multiply substituted or unsubstituted $C_{3-8}$ cycloalkyl; singly or multiply substituted or unsubstituted aryl or heteroaryl; or singly or multiply substituted or unsubstituted aryl, $C_{3-8}$ cycloalkyl or heteroaryl bound by $C_{1-3}$ alkyl; substituted or unsubstituted C(O)phenyl, C(O)heteroaryl, $C(O)C_{1-5}$ alkyl;
- $R^3$ represents saturated or unsaturated, branched or unbranched, singly or multiply substituted or unsubstituted $C_{1-5}$ alkyl; singly or multiply substituted or unsubstituted $C_{3-8}$ cycloalkyl; unsubstituted or singly or multiply substituted aryl or heteroaryl; unsubstituted or singly or multiply substituted aryl, heteroaryl or $C_{3-8}$ cycloalkyl bound by a $C_{1-3}$ alkyl group;
- X represents a branched or unbranched, unsubstituted or singly or multiply substituted alkyl group $(CH_2)_n$, aryl or $C_{3-8}$ cycloalkyl or a substituted or unsubstituted aryl or $C_{3-8}$ cycloalkyl bound by a $C_{1-3}$ alkyl group, where n=0, 1, 2, 3, 4, or 5;
- $R^4$ represents saturated or unsaturated, branched or unbranched, singly or multiply substituted or unsubstituted $C_{1-5}$ alkyl; singly or multiply substituted or unsubstituted $C_{3-8}$ cycloalkyl; singly or multiply substituted or unsubstituted aryl or heteroaryl; or singly or multiply substituted or unsubstituted aryl, $C_{3-8}$ cycloalkyl or heteroaryl bound by $C_{1-3}$ alkyl;

or an acid, base, or physiologically acceptable salt thereof.

2. The cyclohexyl-1,4-diamine compound of claim 1, wherein said compound is present in the form of a pure enantiomer or pure diastereoisomer.

3. The cyclohexyl-1,4-diamine compound of claim 1, wherein said compound is present in the form of a mixture of stereoisomers.

4. The cyclohexyl-1,4-diamine compound of claim 1, wherein said compound is present in the form of a racemic mixture.

5. The cyclohexyl-1,4-diamine compound of claim 1, wherein
$R^1$ and $R^2$ independently of one another represent H; saturated or unsaturated, branched or unbranched, singly or multiply substituted or unsubstituted $C_{1-5}$ alkyl;
or $R^1$ and $R^2$ together form a ring and represent $CH_2CH_2OCH_2CH_2$, $CH_2CH_2NR^{10}CH_2CH_2$ or $(CH_2)_{3-6}$.

6. The cyclohexyl-1,4-diamine compound of claim 1, wherein $R^1$ and $R^2$ independently of one another represent $CH_3$ or H, wherein $R^1$ and $R^2$ do not simultaneously represent H,
or $R^1$ and $R^2$ together form a ring and represent $CH_2CH_2OCH_2CH_2$, $(CH_2)_4$ or $(CH_2)_5$.

7. The cyclohexyl-1,4-diamine compound of claim 1, wherein $R^3$ represents unsubstituted or singly or multiply substituted cyclopentyl, cyclohexyl, phenyl, benzyl, naphthyl, anthracenyl, thiophenyl, benzothiophenyl, furyl, benzofuranyl, benzodioxolanyl, indolyl, indanyl, benzodioxanyl, pyrrolyl, pyridyl, pyrimidyl or pyrazinyl; an unsubstituted or singly or multiply substituted $C_{5-6}$ cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl bound by a saturated, unbranched $C_{1-2}$ alkyl group.

8. The cyclohexyl-1,4-diamine compound of claim 1, wherein $R^3$ represents unsubstituted or singly or multiply substituted phenyl, furyl, thiophenyl, naphthyl, benzyl, benzofuranyl, indolyl, indanyl, benzodioxanyl, benzodioxolanyl, pyridyl, pyrimidyl, pyrazinyl or benzothiophenyl; or unsubstituted or singly or multiply substituted phenyl, furyl or thiophenyl bound by a saturated, unbranched $C_{1-2}$ alkyl group.

9. The cyclohexyl-1,4-diamine compound of claim 1, wherein $R^3$ represents substituted or unsubstituted phenyl, phenethyl, thiophenyl, pyridyl or benzyl.

10. The cyclohexyl-1,4-diamine compound of claim 1, wherein $R^3$ represents phenyl, thienyl, 4-chloro-benzyl, benzyl, 3-chloro-benzyl, 4-methylbenzyl, 2-chloro-benzyl, 4-fluoro-benzyl, 3-methylbenzyl, 2-methylbenzyl, 3-fluoro-benzyl, 2-fluoro-benzyl or phenethyl.

11. The cyclohexyl-1,4-diamine compound of claim 1, wherein $R^4$ represents unsubstituted or singly or multiply substituted $C_{1-5}$ alkyl, cyclohexyl, cyclopentyl, cyclobutyl, cycloheptyl, cyclooctyl, phenyl, benzyl, naphthyl, anthracenyl, thiophenyl, benzothiophenyl, furanyl, isothiazolyl, imidazolyl, triazolyl, triazinyl, pyrazolyl, benzofuranyl, benzodioxolanyl, isoquinolinyl, phthalazine, benzo[1,2,5]thiadiazole, benzothiazole, benzotriazole, quinolinyl, carbazole, isoxazolyl, oxazolyl, indolyl, indanyl, benzodioxanyl, indazolyl, benzimidazolyl, pyrrolyl, pyridyl, pyrimidyl or pyrazinyl; or unsubstituted or singly or multiply substituted phenyl, naphthyl, anthracenyl, thiophenyl, benzothiophenyl, pyridyl, furyl, benzofuranyl, indolyl, indanyl, benzodioxanyl, pyrrolyl, pyrimidyl or pyrazinyl bound by a saturated, unbranched $C_{1-2}$ alkyl group.

12. The cyclohexyl-1,4-diamine compound of claim 1, wherein $R^4$ represents unsubstituted or singly or multiply substituted $C_{1-5}$ alkyl, cyclohexyl, cyclopentyl, phenyl, benzyl, naphthyl, thiophenyl, benzothiophenyl, furanyl, isothiazolyl, imidazolyl, triazolyl, pyrazolyl, benzofuranyl, isoquinolinyl, benzothiazole, benzotriazole, quinolinyl, isoxazolyl, oxazolyl, indolyl, pyrrolyl, pyridyl, pyrimidyl or pyrazinyl; or unsubstituted or singly or multiply substituted benzyl or phenethyl.

13. The cyclohexyl-1,4-diamine compound of claim 1, wherein $R^4$ represents unsubstituted or singly or multiply substituted phenyl, indolyl or methyl.

14. The cyclohexyl-1,4-diamine compound of claim 1, wherein X represents branched or unbranched, unsubstituted or singly or multiply substituted $C_{1-5}$ alkyl, or an unsubstituted or singly or multiply substituted phenyl or $C_{3-8}$ cycloalkyl bound by a branched or unbranched, substituted or unsubstituted $C_{1-3}$ alkyl group.

15. The cyclohexyl-1,4-diamine compound of claim 1, wherein n represents 0.

16. The cyclohexyl-1,4-diamine compound of claim 1, wherein said compound is selected from the group consisting of:

5-oxo-5-phenyl-valeric acid 4-dimethylamino-4-phenyl-cyclohexyl)-amide;
N-(4-dimethylamino-4-thiophen-2-yl-cyclohexyl)-4-(4-fluoro-phenyl)-4-oxo-butyramide;
2-(3-benzofuryl-phenyl)-N-(4-dimethylamino-4-phenethyl-cyclohexyl)-propionamide;
5-oxo-5-phenyl-pentanoic acid (4-dimethylamino-4-phenethyl-cyclohexyl)-amide;
2-(3-benzoyl-phenyl)-N-[4-dimethylamino-4-(2-fluoro-benzyl)-cyclohexyl]-propionamide;
5-oxo-5-phenyl-valeric acid [4-dimethylamino-4-(2-fluoro-benzyl)-cyclohexyl]-amide;
2-(3-benzoyl-phenyl)-N-(4-benzyl-4-dimethylamino-cyclohexyl)-propionamide;
N-[4-dimethylamino-4-(3-fluoro-phenyl)-cyclohexyl]-2-(1H-indol-3-yl)-2-oxo-acetamide;
2-(3-acetyl-2,2-dimethylamino-cyclobutyl)-N-[4-dimethylamino-4-(2-fluoro-benzyl)-cyclohexyl]-acetamide;
2-(3-benzoyl-phenyl)-N-[4-dimethylamino-4-(3-methyl-benzyl)-cyclohexyl]-propionamide;
2-(3-benzoyl-phenyl)-N-[4-dimethylamino-4-(2-methyl-benzyl)-cyclohexyl]-propionamide;
N-[4-(2-chloro-benzyl)-4-dimethylamino-cyclohexyl]-4-(4-chloro-phenyl)-4-oxo-butyramide;
4-oxo-4-phenyl-(4-phenyl-4-piperidin-1-yl-cyclohexyl)-butyramide;
2-(3-acetyl-2,2-dimethylamino-cyclobutyl)-N-[4-dimethylamino-4-(3-methyl-benzyl)-cyclohexyl]-acetamide;
4-(4-fluoro-phenyl)-4-oxo-N-(4-phenyl-4-piperidin-1-yl-cyclohexyl)-butyramide;
2-(3-benzoyl-phenyl)-N-[4-(3-chloro-benzyl)-4-dimethylamino-cyclohexyl]-propionamide;
5-oxo-5-phenyl-valeric acid [4-(3-chloro-benzyl)-4-dimethylamino-cyclohexyl]-amide N-[4-dimethylamino-4-(2-fluoro-benzyl)-cyclohexyl]-4-(4-fluoro-phenyl)-4-oxo-butyramide;
2-(3-benzoyl-phenyl)-N-[4-dimethylamino-4-(4-methyl-benzyl)-cyclohexyl]-propionamide;
N-(4-dimethylamino-4-phenethyl-cyclohexyl)-4-oxo-4-phenyl-butyramide;
N-[4-dimethylamino-4-(2-methyl-benzyl)-cyclohexyl]-4-oxo-4-phenyl-butyramide;
N-[4-dimethylamino-4-(3-methyl-benzyl)-cyclohexyl]-4-oxo-4-phenyl-butyramide;
N-[4-(2-chloro-benzyl)-4-dimethylamino-cyclohexyl]-4-oxo-4-phenyl-butyramide;
5-oxo-5-phenyl-valeric acid (4-phenyl-4-piperidin-1-yl-cyclohexyl)-amide;
2-(3-acetyl-2,2-dimethyl-cyclobutyl)-N-[4-dimethylamino-4-(4-methyl-benzyl)-cyclohexyl]-acetamide;

N-(4-benzyl-4-dimethylamino-cyclohexyl)-4-(4-fluoro-phenyl)-4-oxo-butyramide;
N-[4-dimethylamino-4-(2-fluoro-benzyl)-cyclohexyl]-2-(1H-indol-3-yl)-2-oxo-acetamide;
5-oxo-5-phenyl-valeric acid [4-dimethylamino-4-(4-methyl-benzyl)-cyclohexyl]-amide;
4-(4-chloro-phenyl)-4-dimethylamino-4-(4-fluoro-benzyl)-cyclohexyl]-4-oxo-butyramide;
2-(3-acetyl-2,2-dimethylamino-cyclobutyl)-N-[4-(4-chloro-benzyl)-4-dimethylamino-cyclohexyl]-acetamide;
N-(4-dimethylamino-4-phenethyl-cyclohexyl)-2-(1H-indol-3-yl)-2-oxo-acetamide;
2-(3-acetyl-2,2-dimethyl-cyclobutyl)-N-[4-(3-chloro-benzyl)-4-dimethylamino-cyclohexyl]-acetamide;
N-[4-dimethylamino-4-(4-fluoro-benzyl)-cyclohexyl]-4-oxo-4-phenyl-butyramide;
N-[4-(3-chloro-benzyl)-4-dimethylamino-cyclohexyl]-4-(4-fluoro-phenyl)-4-oxo-butyramide;
2-(3-acetyl-2,2-dimethylamino-cyclobutyl)-N-(4-benzyl-4-piperidin-1-yl-cyclohexyl)-acetamide;
4-(4-chloro-phenyl)-N-[4-dimethylamino-4-(2-methyl-benzyl)-cyclohexyl-4-oxobutyramide;
N-[4-dimethylamino-4-(4-methyl-benzyl)-cyclohexyl]-4-oxo-4-phenyl-butyramide;
N-(4-benzyl-4-dimethylamino-cyclohexyl)-4-(4-chloro-phenyl)-4-oxo-butyramide;
5-oxo-5-phenyl-valeric acid [4-(4-chloro-benzyl)-4-dimethylamino-cyclohexyl]-amide;
4-(4-chloro-phenyl)-N-[4-dimethylamino-4-(4-methyl-benzyl)-cyclohexyl]-4-oxo-butyramide;
N-[4-dimethylamino-4-(3-fluoro-benzyl)-cyclohexyl]-4-(4-fluoro-phenyl)-4-oxo-butyramide;
4-(4-chloro-phenyl)-4-dimethylamino-4-(3-fluoro-benzyl)-cyclohexyl]-4-oxo-butyramide;
2-(3-acetyl-2,2-dimethylamino-cyclobutyl)-N-(4-benzyl-4-dimethylamino-cyclohexyl)-acetamide;
5-oxo-5-phenyl-valeric acid (4-morpholin-4-yl-4-phenyl-cyclohexyl)-amide;
N-[4-dimethylamino-4-(2-methyl-benzyl)-cyclohexyl]-2-(1H-indol-3-yl)-2-oxo-acetamide;
N-[4-dimethylamino-4-(3-methyl-benzyl)-cyclohexyl]-2-(1H-indol-3-yl)-2-oxo-acetamide;
N-[4-dimethylamino-4-(4-fluoro-benzyl)-cyclohexyl]-2-(1H-indol-3-yl)-2-oxo-acetamide;
N-[4-(2-chloro-benzyl)-4-dimethylamino-cyclohexyl]-2-(1H-indol-3-yl)-2-oxo-acetamide;
7-oxo-octanoic acid (4-benzyl-4-dimethylamino-cyclohexyl)-amide;
N-[4-(4-chloro-benzyl)-4-dimethylamino-cyclohexyl]-4-(4-fluoro-phenyl)-4-oxo-butyramide;
4-(4-chloro-phenyl)-N-(4-morpholinyl-4-yl-4-phenyl-cyclohexyl)-4-oxo-butyramide;
N-(4-benzyl-4-piperidin-yl-cyclohexyl)-4-oxo-4-phenyl-butyramide;
N-[4-dimethylamino-4-(4-methyl-benzyl)-cyclohexyl]-4-(4-fluoro-phenyl)-4-oxo-butyramide;
N-(4-benzyl-4-piperidin-1-yl-cyclohexyl)-4-(4-fluoro-phenyl)-4-oxo-butyramide;
7-oxo-octanoic acid [4-dimethylamino-4-(4-methyl-benzyl)-cyclohexyl]-amide;
6-oxo-heptanoic acid [4-(3-chloro-benzyl)-4-dimethylamino-cyclohexyl]-amide;
2-(3-benzoyl-phenyl)-N-(4-benzyl-4-pyrrolidin-1-yl-cyclohexyl)-propionamide;
2-(3-benzoyl-phenyl)-N-(4-phenyl-4-piperidin-1-yl-cyclohexyl)-propionamide;

6-oxo-heptanoic acid [4-(4-chloro-benzyl)-4-dimethylamino-cyclohexyl]-amide;

6-oxo-heptanoic acid (4-morpholin-4-yl-4-phenyl-cyclohexyl)-amide;

4-(4-chloro-phenyl)-N-(4-dimethylamino-4-phenylcyclohexyl)-4-oxobutyramide hydrochloride, non-polar diastereoisomer;

4-(4-chloro-phenyl)-N-(4-dimethylamino-4-phenylcyclohexyl)-4-oxobutyramide hydrochloride, polar diastereoisomer;

5-oxo-5-phenylpentanoic acid (4-dimethylamino-4-phenylcyclohexyl)amide hydrochloride, non-polar diastereoisomer; and 5-oxo-5-phenylpentanoic acid (4-dimethylamino-4-phenylcyclohexyl)amide hydrochloride, polar diastereoisomer.

17. A process for producing a cyclohexyl-1,4-diamine compound according to claim 1, comprising the steps of:
linking a cyclohexane-1,4-diamine with a carboxylic acid corresponding to formula II

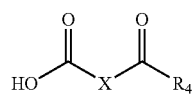

by adding coupling reagents or by activating the carboxylic acid.

18. The process of claim 10, where said process comprises the step of producing an acid chloride.

19. A pharmaceutical formulation comprising at least one cyclohexyl-1,4-diamine compound according to claim 1 and one or more physiologically acceptable auxiliary substances.

20. A method of producing a pharmaceutical formulation comprising the steps of combining a pharmaceutically effective amount of a cyclohexyl-1,4-diamine compound according to claim 1 and one or more physiologically acceptable auxiliary substances.

21. A method of treating pain in a mammal, said method comprising administering to said mammal an effective amount of a compound according to claim 1.

22. The method of claim 21, wherein said pain is acute, neuropathic or chronic pain.

23. A cyclohexyl-1,4-diamine compound corresponding to formula I,

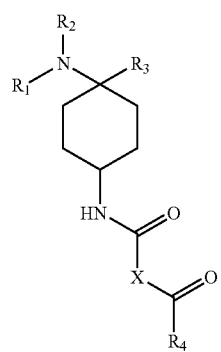

wherein
$R^1$ and $R^2$ independently of one another represent H; saturated or unsaturated, branched or unbranched, singly or multiply substituted or unsubstituted $C_{1-5}$ alkyl; singly or multiply substituted or unsubstituted $C_{3-8}$ cycloalkyl; or singly or multiply substituted or unsubstituted aryl, $C_{3-8}$ cycloalkyl or heteroaryl bound by $C_{1-3}$ alkyl;

or $R^1$ and $R^2$ together represent $CH_2CH_2OCH_2CH_2$, $CH_2CH_2NR^{10}CH_2CH_2$ or $(CH_2)_{3-6}$, wherein $R^{10}$ represents H; saturated or unsaturated, branched or unbranched, singly or multiply substituted or unsubstituted $C_{1-5}$ alkyl; singly or multiply substituted or unsubstituted $C_{3-8}$ cycloalkyl; singly or multiply substituted or unsubstituted aryl or heteroaryl; or singly or multiply substituted or unsubstituted aryl, $C_{3-8}$ cycloalkyl or heteroaryl bound by $C_{1-3}$ alkyl; substituted or unsubstituted $C(O)$phenyl, $C(O)$heteroaryl, $C(O)C_{1-5}$ alkyl;

$R^3$ represents saturated or unsaturated, branched or unbranched, singly or multiply substituted or unsubstituted $C_{1-5}$ alkyl; singly or multiply substituted or unsubstituted $C_{3-8}$ cycloalkyl; unsubstituted or singly or multiply substituted aryl or heteroaryl; unsubstituted or singly or multiply substituted aryl, heteroaryl or $C_{3-8}$ cycloalkyl bound by a $C_{1-3}$ alkyl group;

X represents a branched or unbranched, unsubstituted or singly or multiply substituted alkyl group $(CH_2)_n$, aryl or $C_{3-8}$ cycloalkyl or a substituted or unsubstituted aryl or $C_{3-8}$ cycloalkyl bound by a $C_{1-3}$ alkyl group, where n=0, 1, 2, 3, 4, or 5;

$R^4$ represents saturated or unsaturated, branched or unbranched, singly or multiply substituted or unsubstituted $C_{1-5}$ alkyl; singly or multiply substituted or unsubstituted $C_{3-8}$ cycloalkyl; singly or multiply substituted or unsubstituted aryl or heteroaryl; or singly or multiply substituted or unsubstituted aryl, $C_{3-8}$ cycloalkyl or heteroaryl bound by $C_{1-3}$ alkyl;

or an acid, base, solvate or physiologically acceptable salt thereof.

24. The cyclohexyl-1,4-diamine compound of claim 23, wherein said compound is present in the form of a hydrate.

* * * * *